(12) United States Patent
Keri et al.

(10) Patent No.: US 7,439,252 B2
(45) Date of Patent: Oct. 21, 2008

(54) ASCOMYCIN CRYSTALLINE FORMS AND PREPARATION THEREOF

(75) Inventors: Vilmos Keri, Debrecen (HU); Judith Aronhime, Rehovot (IL); Erzsebet Meszaros Sos, Debrecen (HU); Adrienne Kovacsne-Mezei, Debrecen (HU)

(73) Assignee: TEVA Gyógyszergyár Zártkörúen Müködö Részvénytársaság, Debrecen (HU)

( * ) Notice: Subject to any disclaimer, the term of this patent is extended or adjusted under 35 U.S.C. 154(b) by 87 days.

(21) Appl. No.: 11/293,286

(22) Filed: Dec. 1, 2005

(65) Prior Publication Data

US 2006/0155119 A1    Jul. 13, 2006

Related U.S. Application Data

(60) Provisional application No. 60/633,926, filed on Dec. 6, 2004, provisional application No. 60/632,372, filed on Dec. 1, 2004, provisional application No. 60/641,697, filed on Jan. 5, 2005, provisional application No. 60/641,868, filed on Jan. 5, 2005, provisional application No. 60/641,869, filed on Jan. 5, 2005, provisional application No. 60/709,160, filed on Aug. 17, 2005, provisional application No. 60/705,681, filed on Aug. 3, 2005, provisional application No. 60/662,440, filed on Mar. 16, 2005.

(51) Int. Cl.
*C07D 498/18* (2006.01)
*A61K 31/395* (2006.01)
*A61P 31/04* (2006.01)

(52) U.S. Cl. .................................. 514/291; 540/456

(58) Field of Classification Search ................ 540/456; 514/291
See application file for complete search history.

(56) References Cited

U.S. PATENT DOCUMENTS

| 3,244,592 | A | 4/1966 | Arai et al. |
| 5,359,060 | A | 10/1994 | Hauske |
| 6,423,722 | B1 | 7/2002 | Dosenbach et al. |
| 6,492,513 | B1 | 12/2002 | Nishihara et al. |
| 6,576,135 | B1 | 6/2003 | Higaki et al. |
| 6,881,341 | B2 | 4/2005 | Higaki et al. |
| 2002/0128470 | A1 | 9/2002 | Fuenfschilling et al. |
| 2003/0168409 | A1 | 9/2003 | Higaki et al. |

FOREIGN PATENT DOCUMENTS

| EP | 0 184 162 B1 | 6/1986 |
| EP | 0 323 865 A1 | 6/1989 |
| EP | 0 353 678 A2 | 2/1990 |
| WO | WO 2004/089958 A2 | 10/2004 |
| WO | WO 2005/010015 A1 | 2/2005 |
| WO | WO 2005/019226 A1 | 3/2005 |

OTHER PUBLICATIONS

C.E.M. Griffiths "Ascomycin: An Advance in the Management of Atopic Dermatitis" British J. of Dermatology, V. 144, p. 679-681, (2001).

Z. Song et al. "Highly Chemoselective Trichloracetimidate-Mediated Alkylation of Ascomycin: A Convergent, Practical Synthesis of the Immunosupporessant L-733,725" J. Org. Chem. 1999, v. 64, p. 1859-1867.

*Primary Examiner*—Bruck Kifle
(74) *Attorney, Agent, or Firm*—Kenyon & Kenyon LLP

(57) ABSTRACT

The present invention provides novel crystalline forms of ascomycin as well as processes for the preparation thereof and pharmaceutical compositions comprising such crystalline forms of ascomycin.

55 Claims, 13 Drawing Sheets

Figure 1:
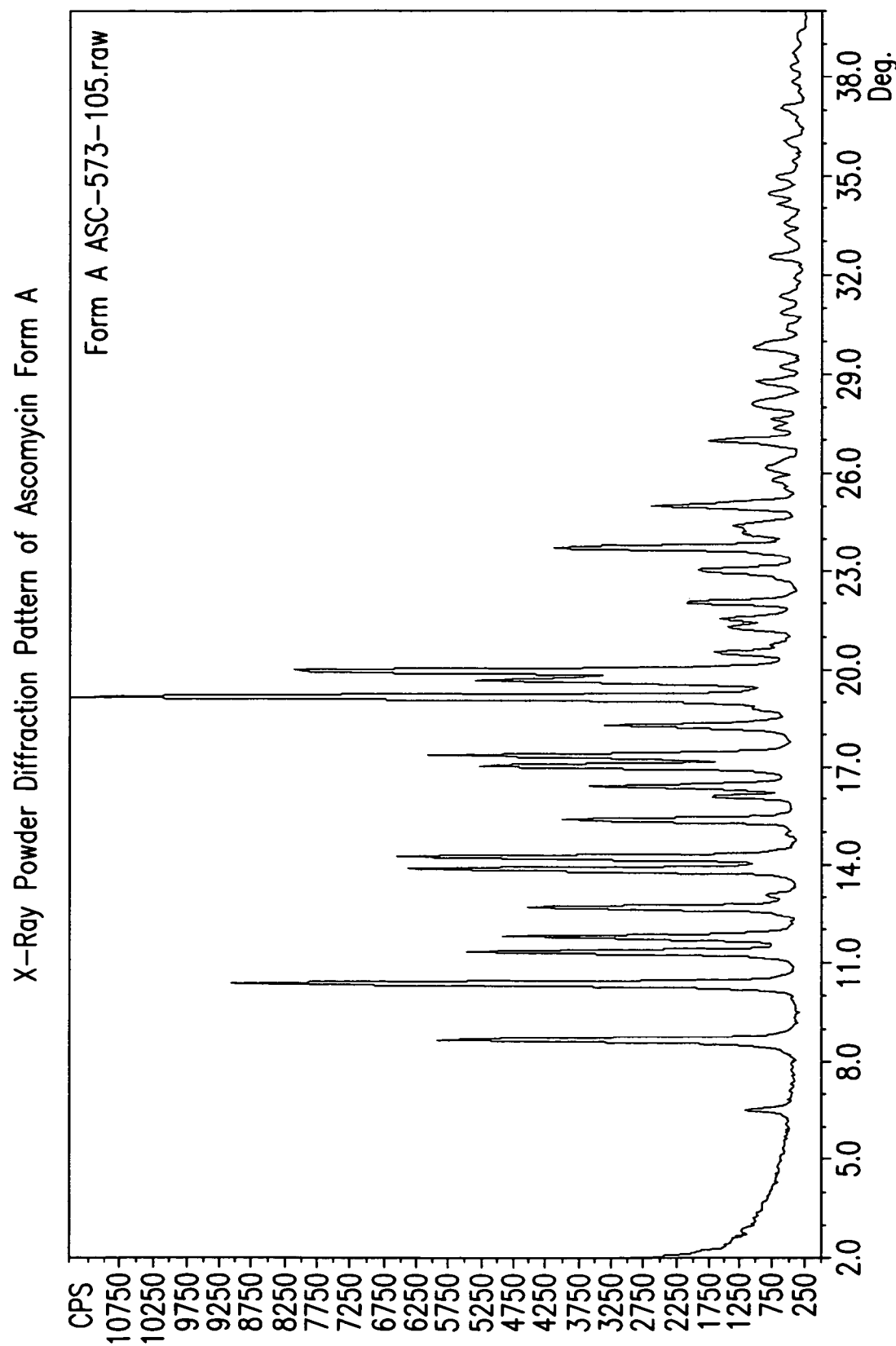

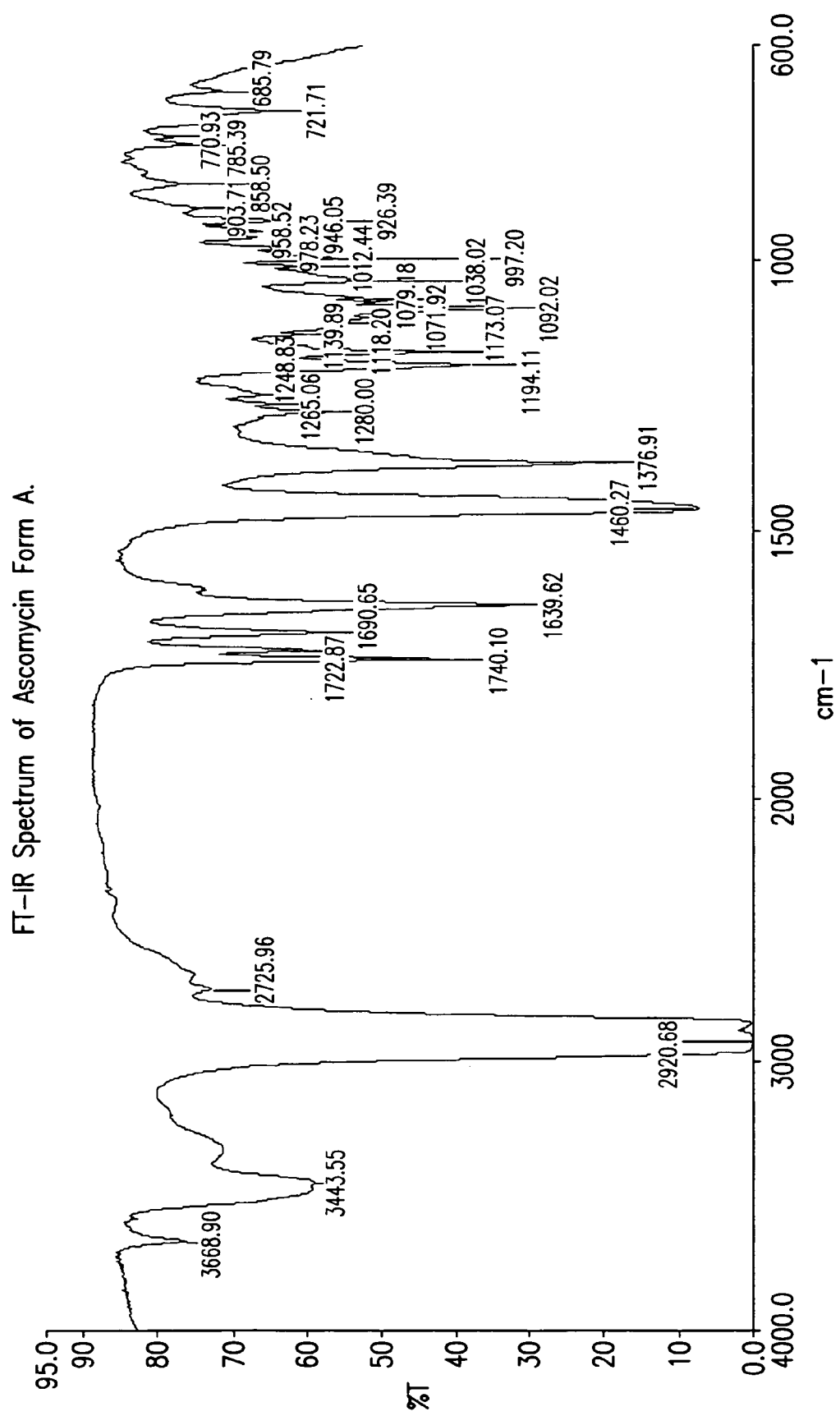
FIG. 10 FT-IR Spectrum of Ascomycin Form A.

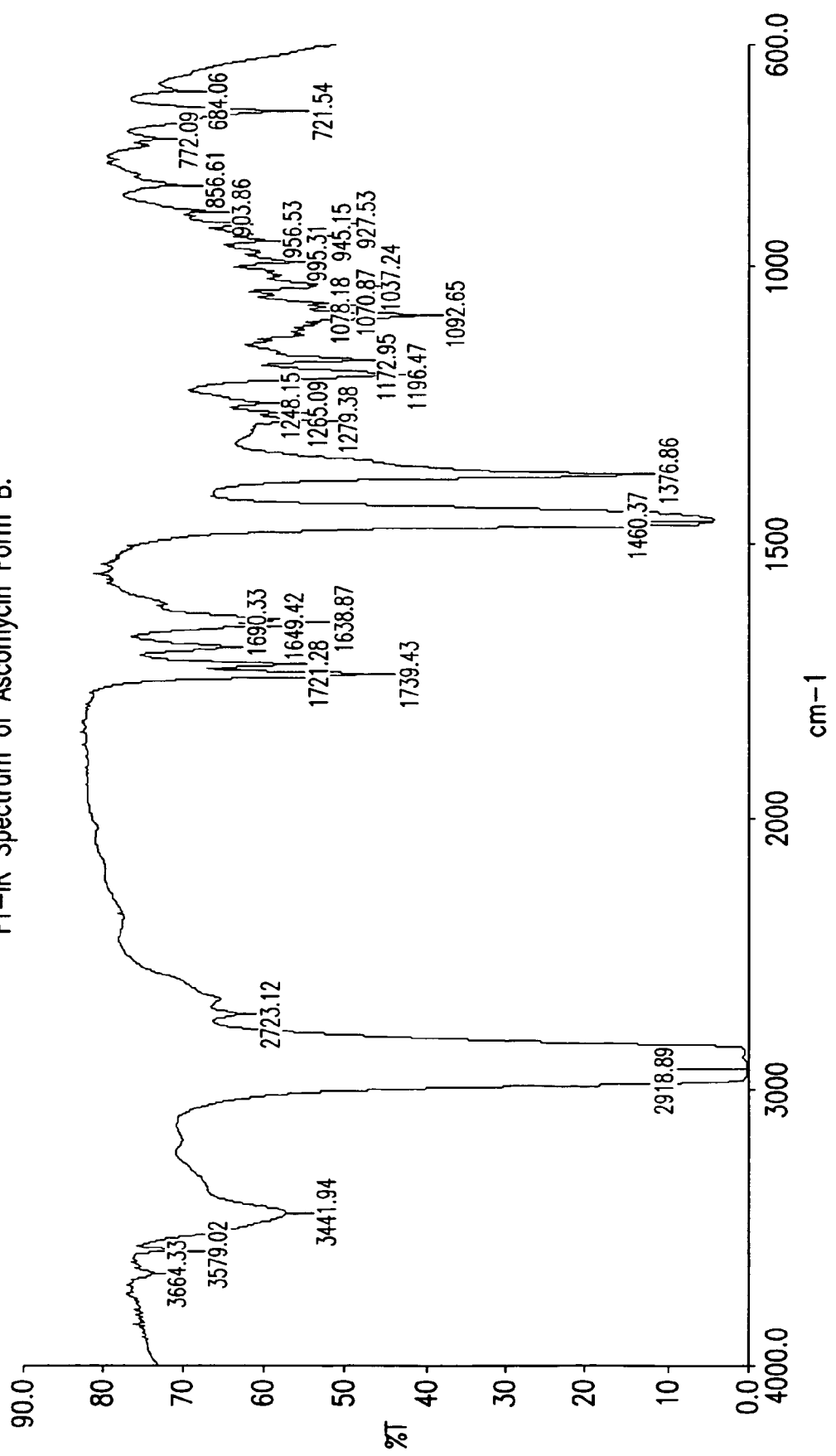

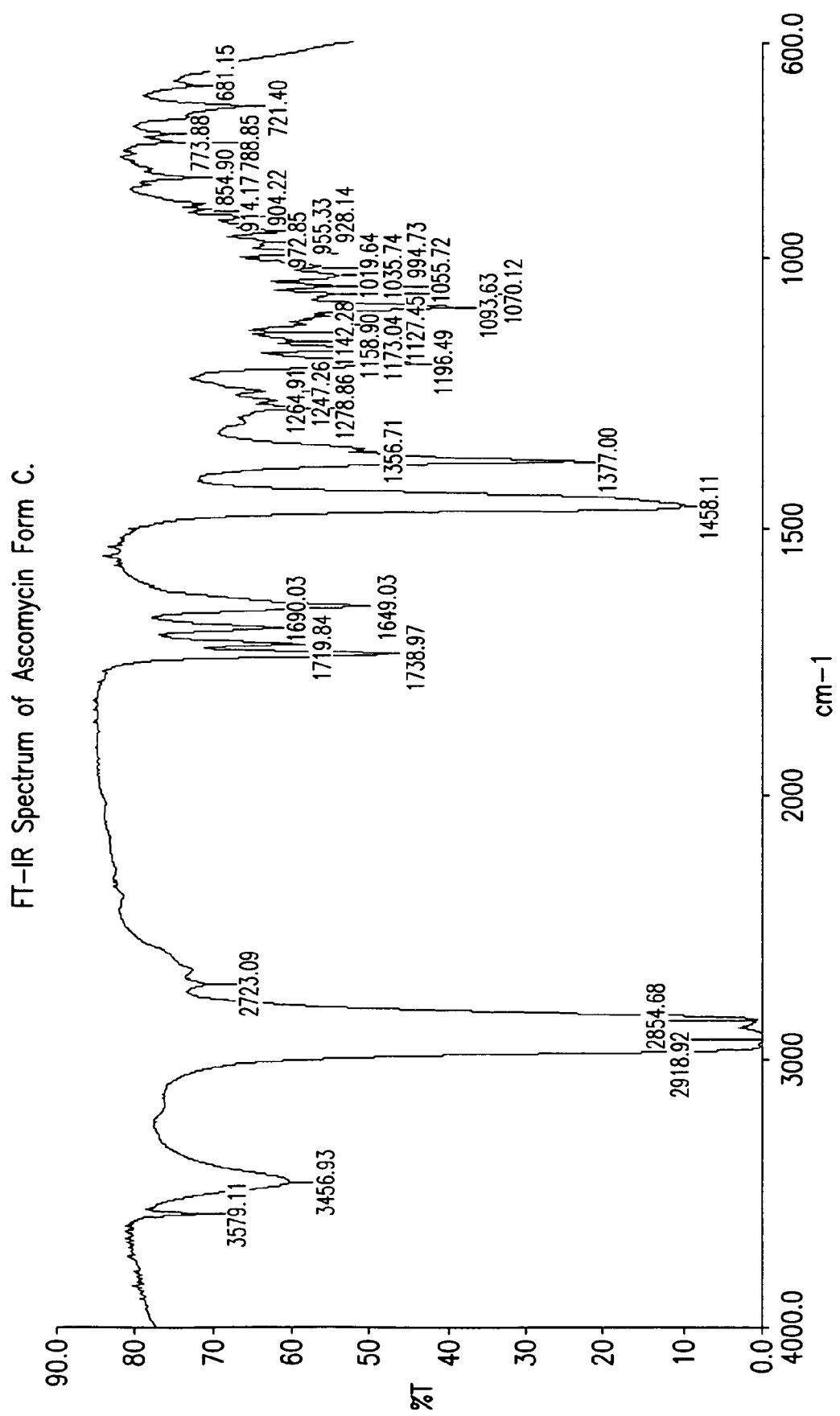

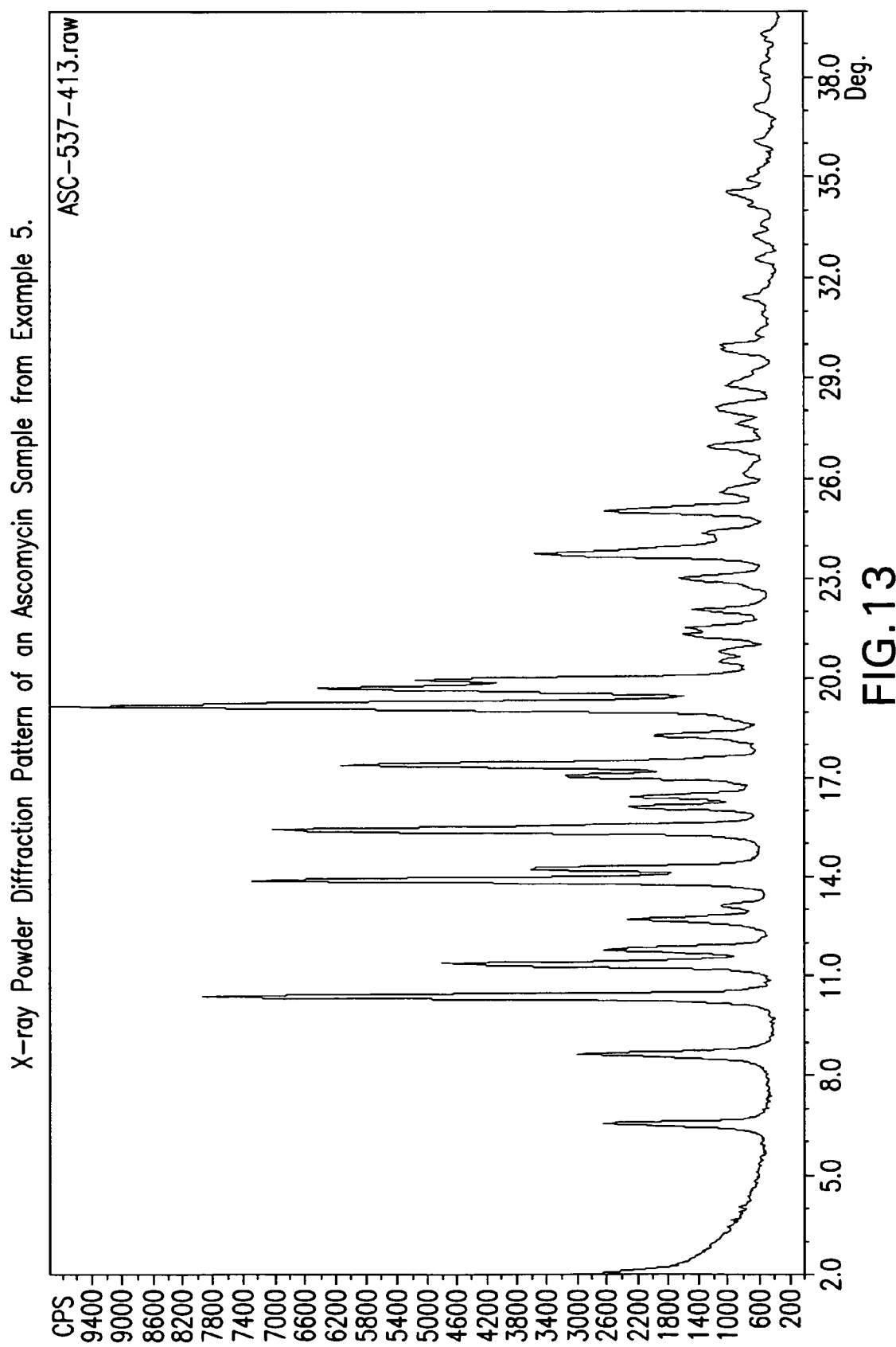

ASCOMYCIN CRYSTALLINE FORMS AND PREPARATION THEREOF

RELATED APPLICATIONS

This application claims benefit of U.S. Provisional Patent Application Nos. 60/632,372, filed Dec. 1, 2004, 60/633,926, filed Dec. 6, 2004, 60/641,697, filed Jan. 5, 2005, 60/641,868, filed Jan. 5, 2005, 60/641,869, filed Jan. 5, 2005, 60/662,440, filed Mar. 16, 2005, 60/705,681, filed Aug. 3, 2005, and 60/709,160, filed Aug. 17, 2005, the contents of which are incorporated herein in their entirety by reference.

FIELD OF THE INVENTION

The present invention is directed to novel crystalline forms of the macrolide Ascomycin and methods of producing these crystalline forms.

BACKGROUND OF THE INVENTION

Macrolides are multi-membered lactone rings having one or more deoxy sugars as substituents. Erythromycin, azithromycin, and clarithromycin are macrolides that have bacteriostatic and/or bactericidal activity. Ascomycin, tacrolimus, and Pimecrolimus are also macrolides.

Ascomycin (CAS No. 11011-38-4) is an immunomodulating macrolactam that reportedly blocks T-cell activation, inhibits cytokine release, and inhibits mast cell activation. "The mechanism of action of ascomycin is very similar to that of cyclosporin and of tacrolimus, although the three compounds have different chemical structures." C. E. Griffiths, Ascomycin: An Advance in the Management of Atopic Dermatitis; Br. J. Dermatol., 144(4), 679-681 (April 2001). Ascomycin was disclosed in U.S. Pat. No. 3,244,592, where the compound is described as an antifungal agent, and it has the chemical formula:

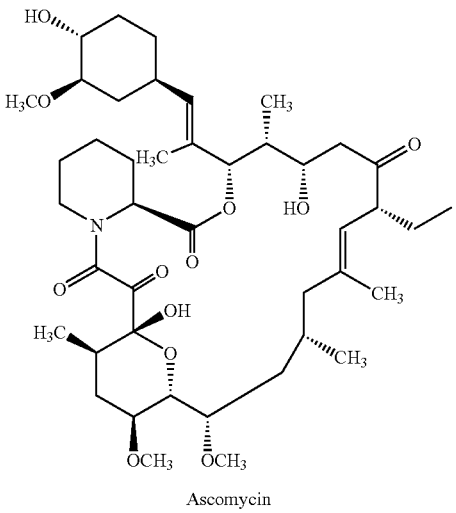

Ascomycin

The use of ascomycin as an immunosuppressant is described in European Patent Application No. 323865.

The crystalline form of a solid chemical compound (or the lack of a crystalline form) affects many of the compound's properties that are important with respect to formulation as a pharmaceutical. Such properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important property of a pharmaceutical compound that may depend on crystallinity is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The solid state form of a compound may also affect its behavior on compaction and its storage stability.

These practical physical characteristics are influenced by the conformation and orientation of molecules in the unit cell, which defines a particular crystalline form of a substance. These conformational and orientation factors in turn result in particular intramolecular interactions such that different crystalline forms may give rise to distinct spectroscopic properties that may be detectable by such analytical techniques as powder X-ray diffraction, solid state $^{13}$C NMR spectrometry, and infrared spectrometry. A particular crystalline form may also give rise to thermal behavior different from that of the amorphous material or another crystalline form. Thermal behavior is measured in the laboratory by such techniques as capillary melting point, thermogravimetric analysis (TGA) and differential scanning calorimetry (DSC) and can be used to distinguish some crystalline forms from others.

The discovery of new crystalline forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. Therefore, there is a need in the art for crystalline forms of Ascomycin.

SUMMARY OF THE INVENTION

The present invention provides a crystalline Ascomycin form, referred to as Form A, and solvates thereof characterized by data selected from: a powder X-ray diffraction pattern with peaks at about 8.7, 11.8 and 14.3±0.2 degrees 2 theta; an FTIR spectra having peaks at about 3443, 1639, 1194 and 1092 cm$^{-1}$; and a DSC thermogram showing two endotherms at about 148-152° C. and at about 158-162° C.

The present invention provides a crystalline Ascomycin form, referred to as Form B, and solvates thereof characterized by data selected from: a powder X-ray diffraction pattern with peaks at about 7.5, 14.7 and 19.2±0.2 degrees 2 theta; an FTIR spectra having peaks at about 3442, 1639, 1196 and 1093 cm$^{-1}$; and a DSC thermogram showing one endothermic peak at about 152-155° C.

The present invention provides a crystalline Ascomycin form, referred to as Form C, and solvates thereof characterized by data selected from: a powder X-ray diffraction pattern with peaks at about 6.6, 15.5 and 19.7±0.2 degrees 2 theta; an FTIR spectra having peaks at about 3459, 1649, 1196 and 1094 cm$^{-1}$; and a DSC thermogram showing one endothermic peak at about 156-160° C.

In preferred embodiments, the novel crystalline forms of ascomycin of the present invention are substantially pure with respect to other crystalline forms of ascomycin, i.e., the novel forms contain less than about 10%, preferably less than about 5%, and even more preferably less than about 1% (by weight) of other crystalline forms of ascomycin. In certain embodiments, the novel crystalline forms contain less than about 10%, preferably less than about 5%, and even more preferably less than about 1% (by weight) of amorphous ascomycin.

The present invention also provides a novel process for preparing crystalline ascomycin comprising:
 a) combining ascomycin with a first polar organic solvent to obtain a solution;
 b) combining the solution with a second polar organic solvent and an antisolvent to form a mixture;
 c) maintaining the mixture until the ascomycin crystallizes; and
 d) recovering crystalline ascomycin.

Preferably, the crystalline ascomycin is Form A or Form C.

The present invention also provides another process for preparing crystalline ascomycin comprising: dissolving ascomycin in ethyl acetate; maintaining the solution at a temperature of about −20° C. to about 10° C.; and recovering crystalline ascomycin.

Preferably, the crystalline ascomycin is Form B.

The present invention further provides a process for preparing ascomycin Form C by maintaining ascomycin Form A at a temperature of about 100° C. to about 160° C. for at least about 30 minutes.

The present invention provides pharmaceutical formulations comprising a therapeutically effective amount of any one of ascomycin Forms A, B or C, and a pharmaceutically acceptable excipient.

The present invention further provides a method for treating a patient suffering from a bacterial infection, atopic dermatitis, or a patient in need of immunosuppressive therapy, comprising the step of administering to the patient the pharmaceutical formulation comprising a therapeutically effective amount of any one of ascomycin Form A, Form B or Form C.

BRIEF DECRIPTION OF THE FIGURES

Figure 2:
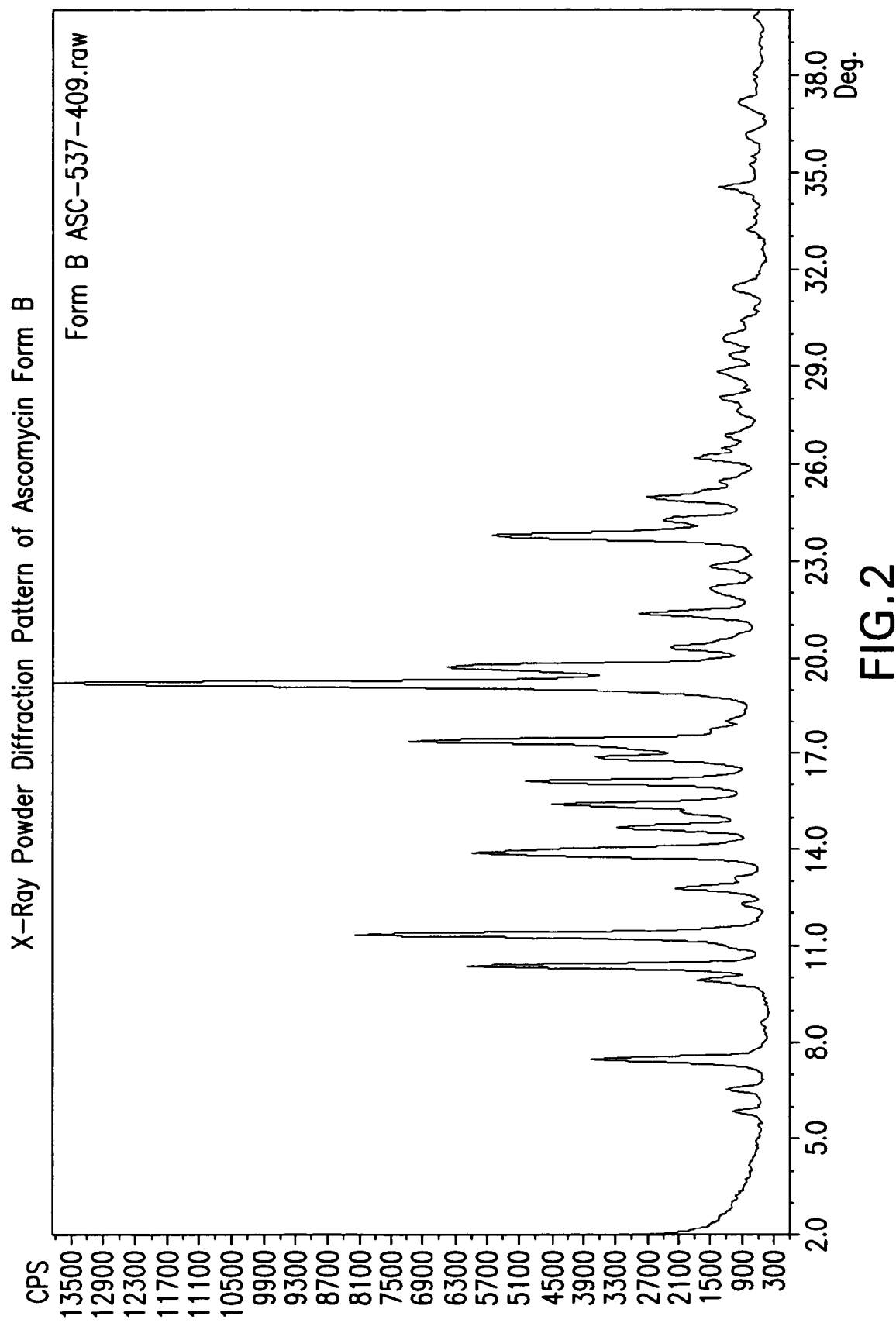
Figure 3:
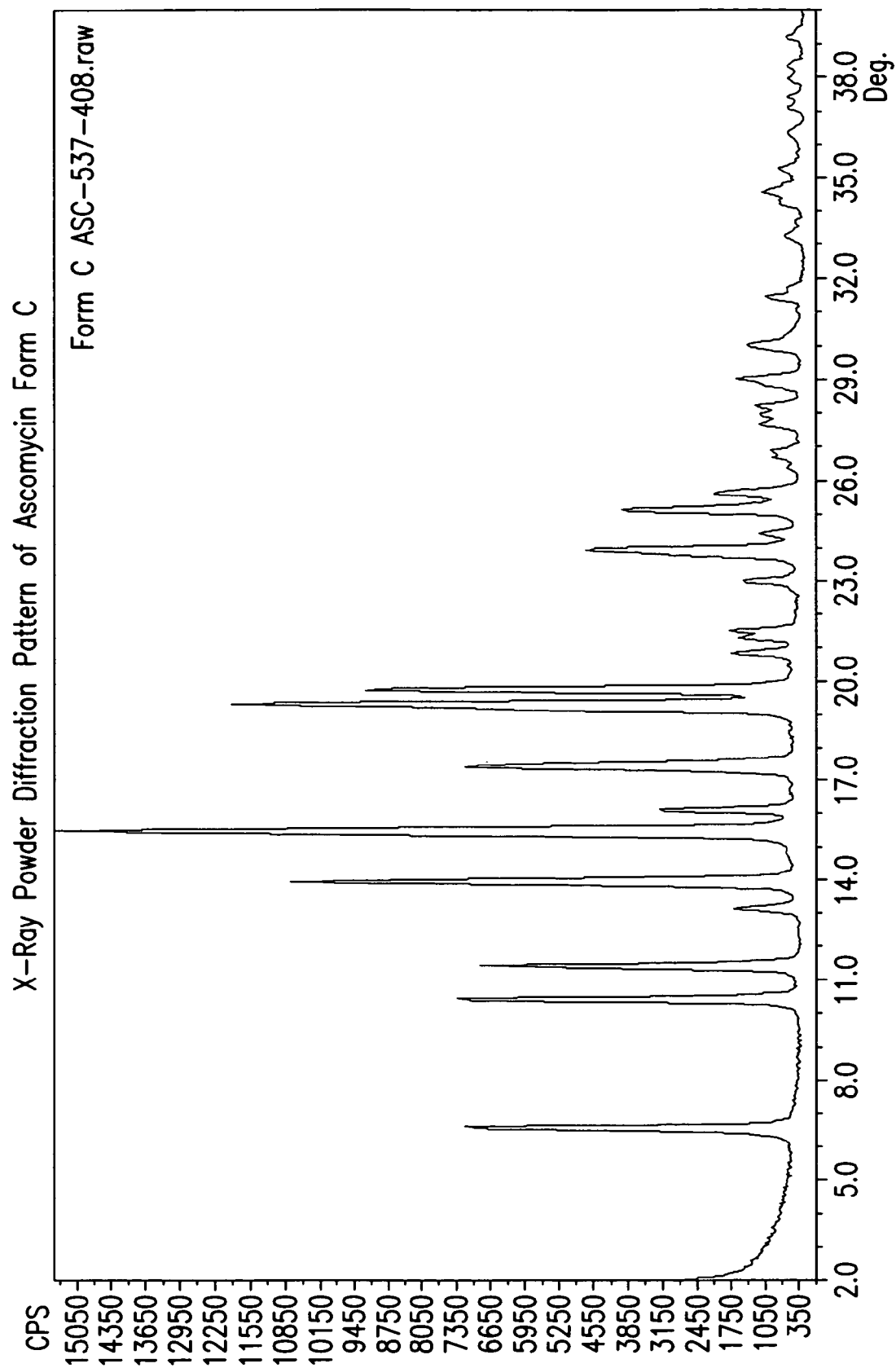
Figure 4:
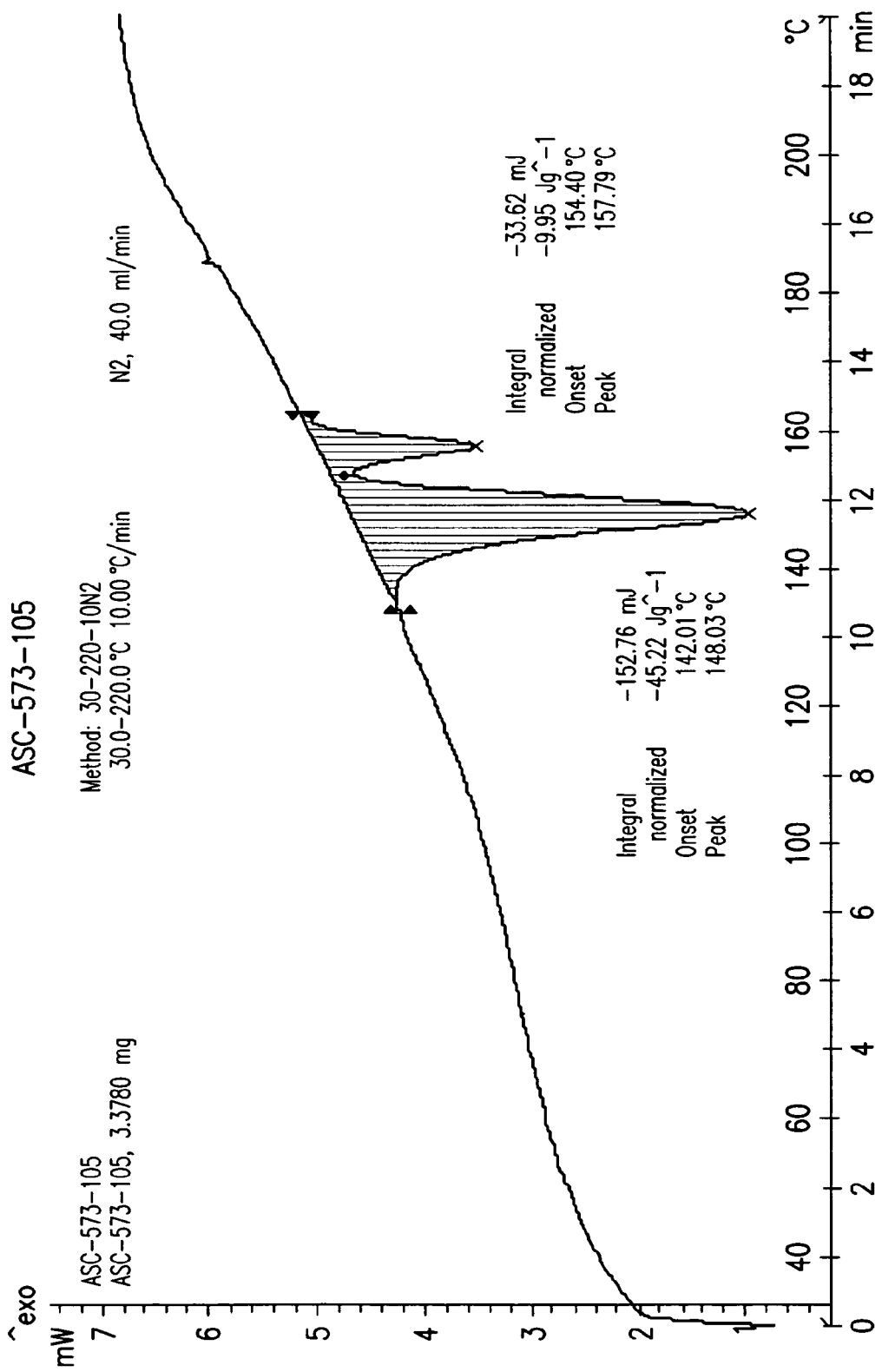
Figure 5:
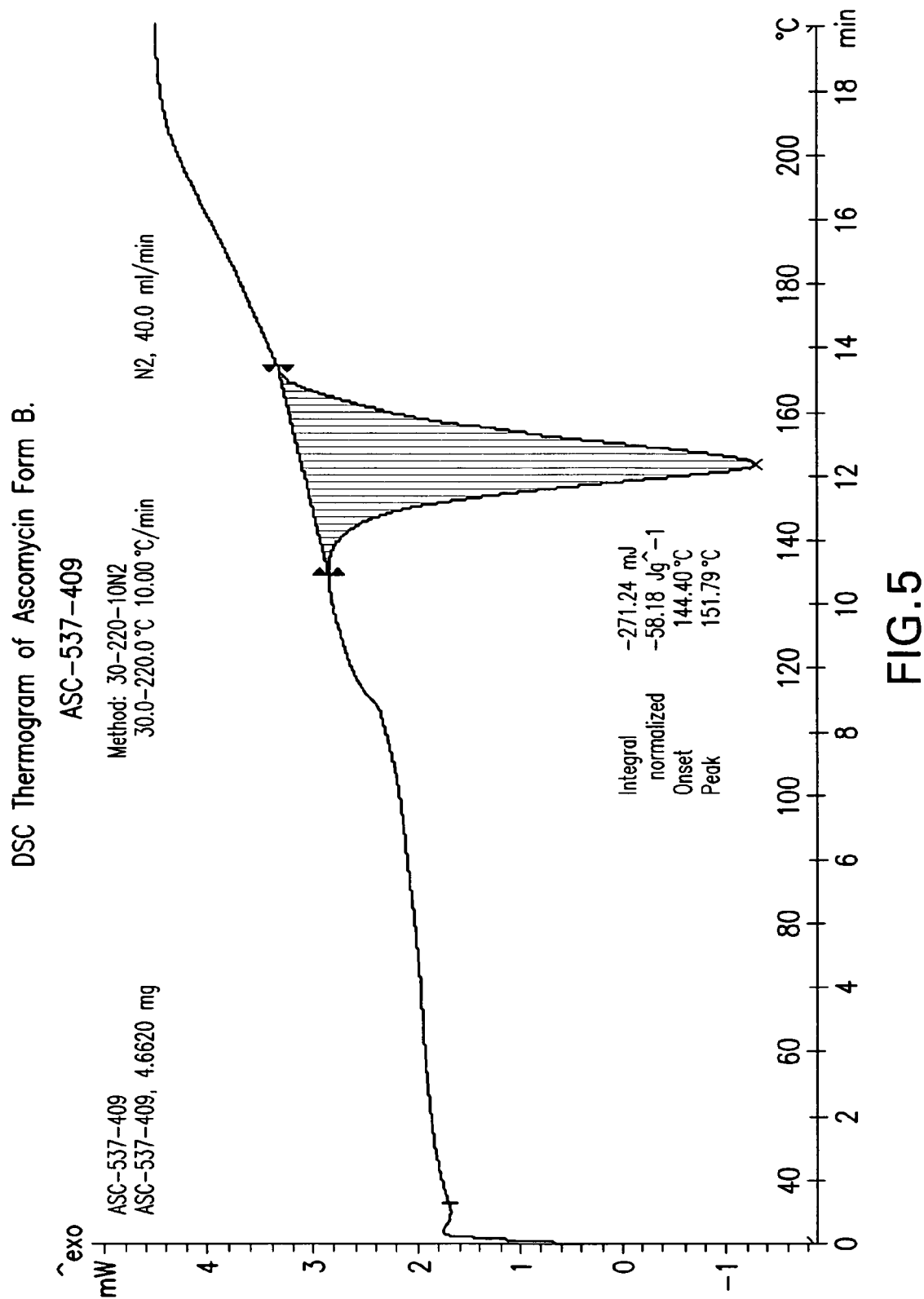
Figure 6:
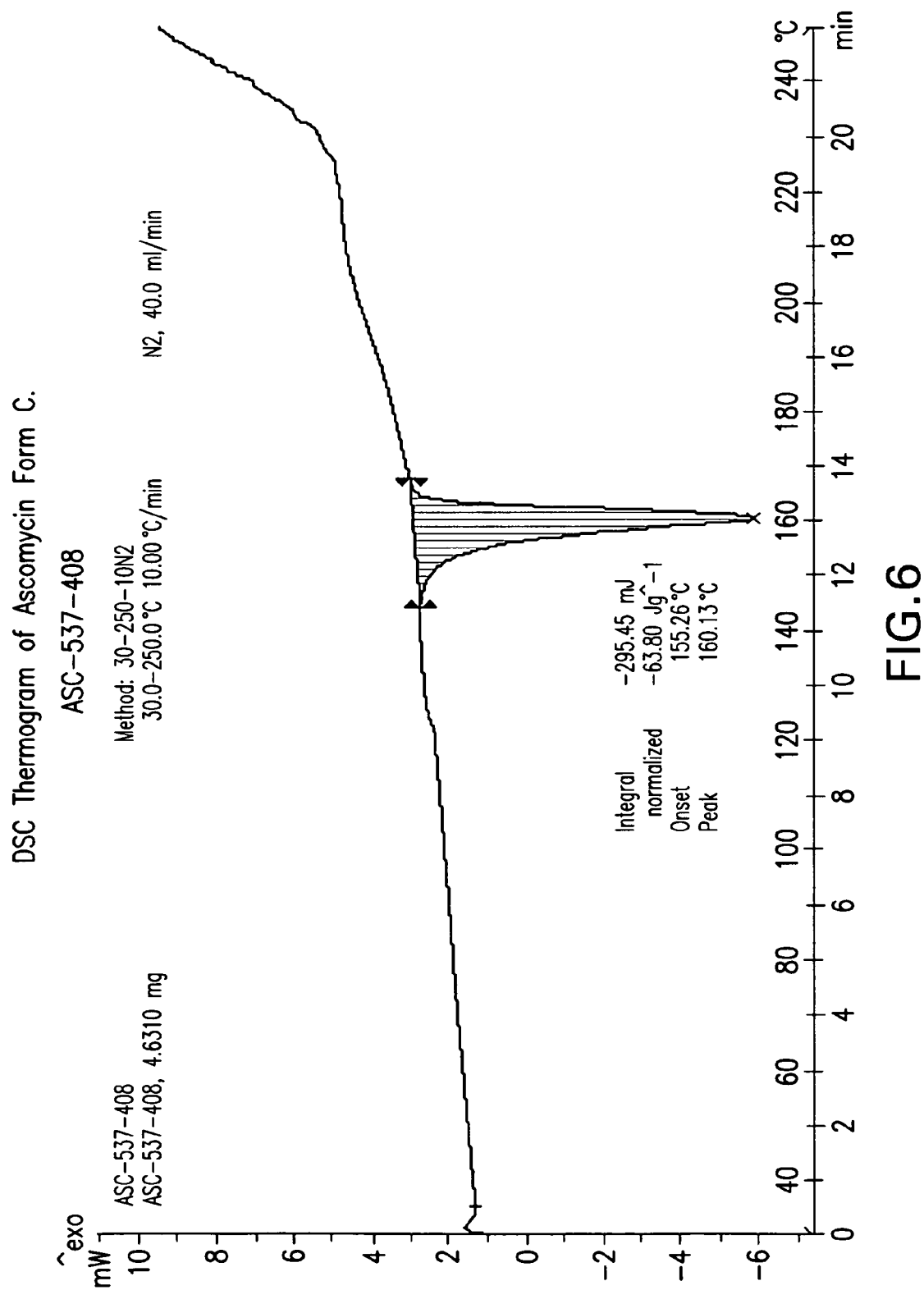
Figure 7:
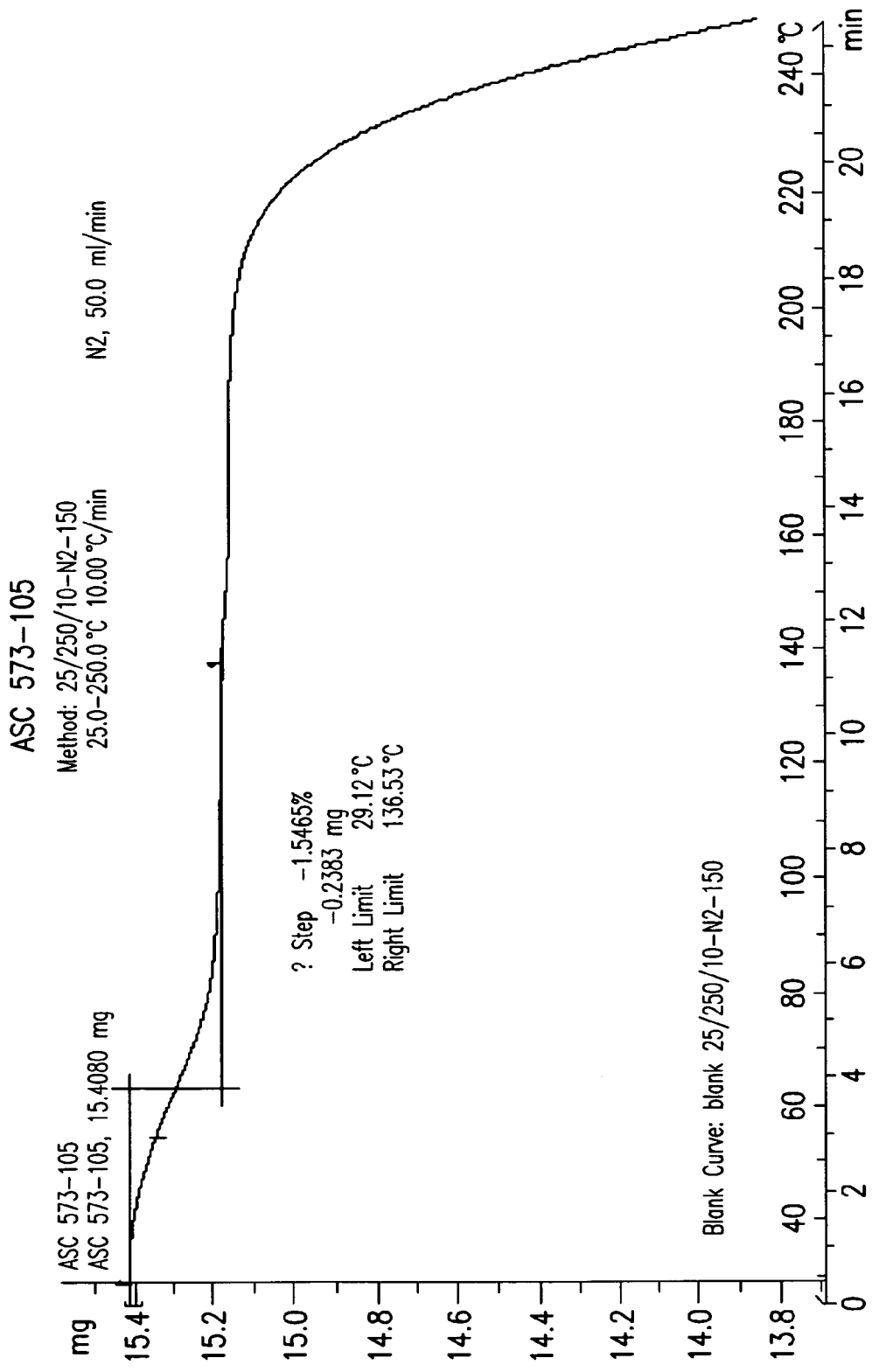
Figure 8:
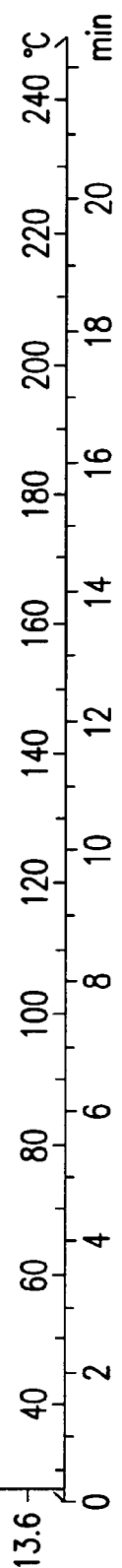
Figure 9:
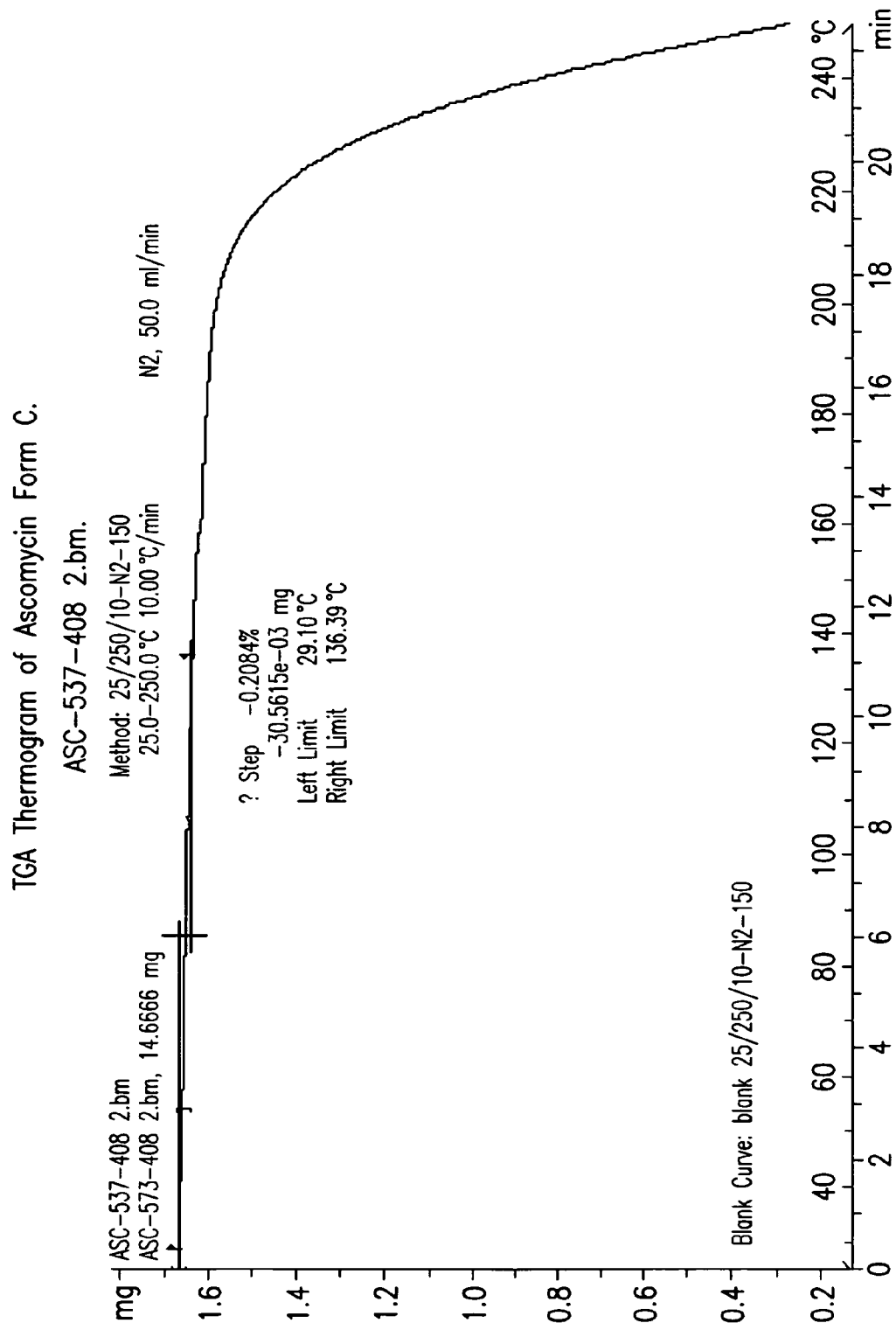

FIG. 1: X-Ray Powder Diffraction pattern of Ascomycin Form A.
FIG. 2: X-Ray Powder Diffraction pattern of Ascomycin Form B.
FIG. 3: X-Ray Powder Diffraction pattern of Ascomycin Form C.
FIG. 4: DSC thermogram of Ascomycin Form A.
FIG. 5: DSC thermogram of Ascomycin Form B.
FIG. 6: DSC thermogram of Ascomycin Form C.
FIG. 7: TGA thermogram of Ascomycin Form A.
FIG. 8: TGA thermogram of Ascomycin Form B.
FIG. 9: TGA thermogram of Ascomycin Form C.
FIG. 10: FT-IR spectrum of Ascomycin Form A.
FIG. 11: FT-IR spectrum of Ascomycin Form B.
FIG. 12: FT-IR spectrum of Ascomycin Form C.
FIG. 13. X-ray Powder Diffraction pattern of an Ascomycin sample from Example 5.

DETAILED DESCRIPTION

As used herein, the term "room temperature" refers to a temperature of about 15° C. to about 30° C., preferably about 18° C. to about 25° C.

By "small amount" of polar solvent is meant a ratio of solvent mixture to polar solvent (or mixture of two or more polar solvents) of about 140/1 to about 636/1, preferably about 200/1 to about 500/1, even more preferably about 300/1 to about 350/1, on a volume/volume basis. Ratios of solvent mixture/polar solvent (or polar solvent mixture) that have been found to be suitable include: 140/1, 212/1, 300/1, 318/1, 325/1, 350/1, and 636/1.

Alternatively, a "small amount" can be considered with respect to the ratio of the molar equivalents of polar solvent (or polar solvent mixture) to macrolide. It has been found that as little as 0.5 molar equivalents of polar solvent with respect to macrolide results in the crystallization of the macrolide. Thus, it is within the scope of the present invention to add about 0.3, 0.4, 0.5, 0.6, 0.7, or 0.8 (or sometimes even more) molar equivalents of polar solvent (with respect to macrolide) in the processes of the present invention to effect crystallization of the macrolide.

The present invention provides a crystalline Ascomycin form, referred to as Form A, and solvates thereof characterized by data selected from: a powder X-ray diffraction pattern with peaks at about 8.7, 11.8 and 14.3±0.2 degrees 2 theta; an FTIR spectra having peaks at about 3443, 1639, 1194 and 1092 cm$^{-1}$; and a DSC thermogram showing two endotherms at about 148-152° C. and at about 158-162° C.

Ascomycin Form A may be further characterized by a powder X-ray diffraction pattern with peaks at about 8.7, 10.4, 11.4, 11.8, 12.7, 13.9, 14.3, 17.1, 17.4, 19.2, and 20.0 ±0.2 degrees 2 theta (substantially as depicted in FIG. 1). Form A may be also characterized by an FTIR spectra having additional peaks at about 3665, 1740, 1723, 1691, 1640, 1280, 1194, 1173, 1038, 997, 926, 858, 785, 771, 722 and 686 cm$^{-1}$ (substantially as depicted in FIG. 10). Furthermore, ascomycin Form A may be characterized by a DSC thermogram substantially as depicted in FIG. 4.

The weight loss until melting measured by TGA of Ascomycin crystalline Form A is about 1.6-1.8%, which corresponds to the water content determined by Karl Fischer titration (substantially as depicted in FIG. 7).

Ascomycin crystalline Form A of the present invention has rod shaped particles that form aggregates. A preferred maximum particle size is of about 60 μm.

The present invention provides a crystalline Ascomycin form, referred to as Form B, and solvates thereof characterized by data selected from: a powder X-ray diffraction pattern with peaks at about 7.5, 14.7 and 19.2±0.2 degrees 2 theta; a FTIR spectra having peaks at about 3442, 1639, 1196 and 1093 cm$^{-1}$; and a DSC thermogram showing one endothermic peak at about 152-155° C.

Ascomycin Form B may be further characterized by a powder X-ray diffraction pattern with peaks at about 7.5, 10.4, 11.4, 13.9, 14.7, 15.4, 16.2, 17.4, 19.2, 19.7, 21.4 and 23.8±0.2 degrees 2 theta (substantially as depicted in FIG. 2). Form B may be also characterized by an FTIR spectra having peaks at about 3579, 3442, 1739, 1721, 1690, 1649, 1639, 1279, 1197, 1173, 1093, 1037, 996, 928, 857 and 722 cm$^{-1}$ (substantially as depicted in FIG. 11). Furthermore, ascomycin Form B may be characterized by a DSC thermogram substantially as depicted in FIG. 5.

The weight loss until melting measured by TGA of Ascomycin crystalline Form B is about 1.0-1.2%, which corresponds to the water content determined by Karl fischer titration (substantially as depicted in FIG. 8).

Ascomycin crystalline Form B of the present invention has rod shaped particles that form aggregates. A preferred maximum particle size is of about 100 μm.

The present invention provides a crystalline Ascomycin form, referred to as Form C, and solvates thereof characterized by data selected from: a powder X-ray diffraction pattern with peaks at about 6.6, 15.5 and 19.7±0.2 degrees 2 theta; a FTIR spectra having peaks at about 3459, 1649, 1196 and 1094 cm$^{-1}$; and a DSC thermogram showing one endothermic peak at about 156-160° C.

Ascomycin Form C may be further characterized by a powder X-ray diffraction pattern with peaks at about 6.6, 10.4, 11.4, 13.9, 15.4, 17.4, 19.3, 19.7, 23.9, 25.1 and 25.6 ±0.2 degrees 2 theta (substantially as depicted in FIG. 3). Form C may be also characterized by an FTIR spectra having peaks at about 3579, 3457, 1739, 1720, 1690, 1649, 1279, 1196, 1094, 1036, 995, 955, 928, 855, 789, 774, 721 and 682 cm$^{-1}$ (substantially as depicted in FIG. 12). Furthermore, ascomycin Form C may be characterized by a DSC thermogram substantially as depicted in FIG. 6.

The weight loss until melting measured by TGA of Ascomycin crystalline Form C is less than 0.3%, which corresponds to the water content determined by Karl Fischer titration (substantially as depicted in FIG. 9). Ascomycin crystalline Form C is an anhydrate.

Ascomycin crystalline Form C of the present invention has rod shaped particles and plates that form aggregates. A preferred maximum particle size is of about 40 to about 50 µm.

The novel crystalline forms of ascomycin of the present invention are substantially pure with respect to other crystalline forms of ascomycin, i.e., the novel forms contain less than about 10%, preferably less than about 5%, and even more preferably less than about 1% (by weight) of other crystalline forms of ascomycin. In certain embodiments, the novel crystalline forms contain less than about 10%, preferably less than about 5%, and even more preferably less than about 1% (by weight) of amorphous ascomycin.

The present invention also provides a novel process for preparing crystalline ascomycin comprising:
 a) combining ascomycin with a first polar organic solvent to obtain a solution;
 b) combining the solution with a second polar organic solvent and an antisolvent to form a mixture;
 c) maintaining the mixture until ascomycin crystallizes; and
 d) recovering crystalline ascomycin.

Preferably, the crystalline ascomycin is Form A or Form C.

Preferably, the first polar organic solvent in step a) is selected from the group consisting of: ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methy-ethyl ketone, and mixtures thereof. Most preferably, the first polar organic solvent is ethyl acetate.

In order to obtain a clear solution, the temperature in step a) is elevated to not more than about 50° C.

Alternatively, a clear solution may be obtained by diluting or filtering out any particle. Filtration may be done through paper, glass fiber or other membrane material, or a clarifying agent such as celite. Depending upon the equipment used and the concentration and temperature of the solution, the filtration apparatus may need to be preheated to avoid premature crystallization.

Preferably, the antisolvent is selected from the group consisting of: cyclohexane, hexane, heptane, n-octane, iso-octane, and methylcyclohexane. Most preferably, the antisolvent is cyclohexane.

Optionally, the process may be performed without the antisolvent of step b).

Preferably, the second polar organic solvent is selected from the group consisting of: water, N,N-dimethylformamide, dimethylsulfoxide, dimethyl acetamide, N,N-diethylformamide, and mixtures thereof. More preferably, the polar solvent is selected from the group consisting of: water, N,N-dimethylformamide, and dimethylsulfoxide. Most preferably, the polar solvent is water or N,N dimethylformamide.

Optionally, the polar solvent is added in a small amount.

Preferably, the antisolvent and the polar solvent are added more or less simultaneously to the solution of ascomycin in the solvent.

Preferably, the reaction mixture in step c) is maintained at a low temperature to induce crystallization. Preferably the reaction mixture is maintained at a temperature of about −15° C. to about 30° C. Preferably, the reaction mixture is maintained at a temperature of about 0° C. to about 8° C.

The crystallization is facilitated by initially using a concentrated solution of ascomycin. Preferably, the solution concentration is about 0.06 g/mL to about 0.8 g/mL. A high concentration also results in a higher yield.

The present invention also provides another process for preparing crystalline ascomycin comprising: dissolving ascomycin in ethyl acetate; maintaining the solution at a temperature of about −20° C. to about 10° C.; and recovering crystalline ascomycin. Preferably, the crystalline ascomycin obtained by this process is Form B.

Preferably, the solution is maintained at a temperature of about 0° C. to about 8° C.

The present invention further provides a process for preparing ascomycin Form C by maintaining ascomycin Form A at a temperature of about 100° C. to about 160° C. for at least about 30 minutes. Preferably, Form A is maintained at a temperature of about 150° C. Preferably, Form A is maintained for about 1 hour.

The present invention provides a pharmaceutical formulation comprising a therapeutically effective amount of any one of ascomycin Form A, Form B or Form C, and an amount of at least one pharmaceutically acceptable excipient.

"Therapeutically effective amount" means the amount of a crystalline form that, when administered to a patient for treating a disease or other undesirable medical condition, is sufficient to have a beneficial effect with respect to that disease or condition. The "therapeutically effective amount" will vary depending on the crystalline form, the disease or condition and its severity, and the age, weight, etc., of the patient to be treated. Determining the therapeutically effective amount of a given crystalline form is within the ordinary skill of the art and requires no more than routine experimentation.

The present invention also provides a method for treating a patient suffering from a bacterial infection, comprising the step of administering to the patient the pharmaceutical formulation comprising a therapeutically effective amount of Ascomycin selected from the group consisting of any of the above mentioned crystalline forms of Ascomycin. A further embodiment of the present invention is a method for treating a patient suffering from atopic dermatitis, comprising the step of administering to the patient the pharmaceutical formulation comprising a therapeutically effective amount of Ascomycin selected from the group consisting of any of the above mentioned crystalline forms of Ascomycin. A still further embodiment of the present invention is a method for treating a patient in need of immunosuppressive therapy, comprising the step of administering to the patient the pharmaceutical formulation comprising a therapeutically effective amount of Ascomycin selected from the group consisting of any of the above mentioned crystalline forms of Ascomycin.

The crystalline forms of the present invention used to prepare pharmaceutical formulations may be substantially pure with respect to other crystalline forms, i.e., the novel forms contain less than about 10%, preferably less than about 5%, and even more preferably less than about 1% (by weight) of other crystalline forms of Ascomycin. In certain embodiments, the novel crystalline forms contain less than about 10%, preferably less than about 5%, and even more preferably less than about 1% (by weight) of amorphous Ascomycin.

Pharmaceutical formulations of the present invention contain crystalline Ascomycin, such as one of the crystalline forms disclosed herein, optionally in a mixture with other forms of Ascomycin. In addition to the active ingredient(s), the pharmaceutical formulations of the present invention may contain one or more excipients. Excipients are added to the formulation for a variety of purposes.

Diluents may be added to the formulations of the present invention. Diluents increase the bulk of a solid pharmaceutical composition, and may make a pharmaceutical dosage form containing the composition easier for the patient and caregiver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

The present invention is not intended to encompass true solutions of Ascomycin whereupon the crystal structure of the novel crystalline forms and the properties that distinguish the novel crystalline forms of Ascomycin of the present invention are lost. Thus, the pharmaceutical compositions of the present invention comprising the novel crystalline forms of Ascomycin disclosed herein will primarily be solid pharmaceutical compositions. However, the use of the novel forms to prepare such solutions (e.g., so as to deliver Ascomycin in a liquid pharmaceutical formulation) is considered to be within the contemplation of the invention.

In liquid pharmaceutical compositions prepared using the crystalline forms of the present invention, Ascomycin and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The oral dosage form of the present invention is preferably in the form of an oral capsule having a dosage of about 10 mg to about 160 mg, more preferably from about 20 mg to about 80 mg, and most preferably capsules of 20, 40, 60 and 80 mg. Daily dosages may include 1, 2, or more capsules per day.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting. A capsule filling of the present invention may comprise any of the aforementioned blends and granulates that were described with reference to tableting, however, they are not subjected to a final tableting step.

The active ingredient and excipients may be formulated into compositions and dosage forms according to methods known in the art.

It is not necessary that the formulations of the present invention contain only one crystalline form of Ascomycin. The crystalline forms of the present invention may be used in pharmaceutical formulations or compositions as single components or mixtures together with other crystalline forms of Ascomycin or with amorphous Ascomycin. However, it is preferred that the pharmaceutical formulations or compositions of the present invention contain 25-100% by weight, especially 50-100% by weight, of at least one of the novel forms, based on the total amount of Ascomycin in the formulation or composition.

Preferably, such an amount of the novel crystalline form of Ascomycin is 75-100% by weight, especially 90-100% by weight. Highly preferred is an amount of 95-100% by weight.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Instruments

The crystalline forms of ascomycin, produced by the methods of the present invention can be analyzed by Powder X-ray diffraction (PXRD) was performed on an X-Ray powder diffractometer, ARL, θ-θ goniometer, Cu-tube, solid state detector with Peltier cooling. The sample holder was a round standard aluminum sample holder with round zero background. Scanning parameters: Range: 2-40 deg.2θ, Continuous Scan, Rate: 3 deg./min.

Ascomycin crystalline forms can also be analyzed by thermal analysis, which can be carried out by digital scanning calorimetry (DSC) and by thermogravimetric analysis (TGA). DSC thermograms can be obtained on a DSC822$^e$ Mettler Toledo instrument (Advanced Instruments, San Juan, Puerto Rico). Sample weight: 3-5 mg; Heating rate: 10° C./min; Number of holes in the crucible: 3. TGA thermograms can be obtained on a Mettler TGA/SDTA 851 instrument (Advanced Instruments, San Juan, Puerto Rico) using a standard Allumina pan. Sample weight: 7-15 mg; Heating rate: 10° C./min.

The particle size may be measured by the following methods: sieves, sedimentation, electrozone sensing (coulter counter), microscopy, Low Angle Laser Light Scattering (LALLS).

Example 1

Process for Preparation of Ascomycin Form A

Crystalline Ascomycin Form A (150.1 g) was dissolved in ethyl acetate (1000 ml) and evaporated to dryness. This process was repeated twice. The evaporated oily material was dissolved in ethyl acetate (300 ml). Cyclohexane (1800 ml) was added to the solution. Water (3.3 ml) was added in small portions during 3 hours. The mixture was stirred for an hour at room temperature. The crystalline product thus formed was filtered and washed with cyclohexane (300 ml) and dried for 1.5 hour at 70° C. under vacuum. Ascomycin Form A (133.6 g) was obtained.

Example 2

Process for Preparation of Ascomycin Form B

Ascomycin crude product (6 g) was dissolved in ethyl acetate (48 ml) and evaporated to reduced volume (9 ml). The mixture was stirred at room temperature for an hour and then incubated at 0-8° C. for 24 hours. The crystalline product thus formed was filtered and washed with cyclohexane (18 ml) and dried for 1.5 hours at 70° C. under vacuum. Ascomycin Form B (3.51 g) was obtained.

Example 3

Process for Preparation of Ascomycin Form C

Ascomycin crude product (6 g) was dissolved in ethyl acetate (60 ml) and evaporated to dryness. This process was repeated twice. The evaporated oily material was dissolved in ethyl acetate (6 ml). Cyclohexane (36 ml) and dimethyl formamide (0.12 ml) were added to the solution and it was stirred for 1.5 hours at room temperature. The crystalline product thus formed was filtered and washed with cyclohexane (18 ml) and dried for 1 hour at 70° C. under vacuum. Ascomycin Form C (2.76 g) was obtained.

Example 4

Process for Preparation of Ascomycin Form C

Crystalline Ascomycin Form A (6 g) was dissolved in ethyl acetate (60 ml) and evaporated to dryness. This process was repeated twice. The evaporated oily material was dissolved in ethyl acetate (6 ml). Cyclohexane (66 ml) and dimethyl sulfoxide (0.24 ml) were added to the solution and it was stirred for 1.5 hours at room temperature. The crystalline product thus formed was filtered and washed with cyclohexane (18 ml) and dried for 1 hour at 70° C. under reduced pressure. Ascomycin Form C (4.81 g) was obtained.

Example 5

Process for Preparation of Ascomycin

Crystalline Ascomycin Form A (6 g) was dissolved in ethyl acetate (60 ml) and evaporated to dryness. This process was repeated twice. The evaporated oily material was dissolved in ethyl acetate (6 ml). Cyclohexane (36 ml) and a mixture of dimethyl formamide (0.06 ml) and water (0.06 ml) was added to the solution. The mixture was stirred for 1.5 hours at room temperature. The crystalline product was filtered and washed with cyclohexane (18 ml) and dried for 1 hour at 70° C. under reduced pressure. Ascomycin Form A (5.46 g) was obtained.

Example 6

Process for Preparation of Ascomycin Form C at 150° C.

Starting from Form A having the properties listed in Table 1, incubation at 150° C. for 1 hour produced Ascomycin Form C.

TABLE 1

| | Initial | | | After storing at 150° C. for 1 hour | | |
|---|---|---|---|---|---|---|
| Sample | PXRD | DSC ° C., J/g | Water content (%) | PXRD | DSC ° C., J/g | remarks |
| | A | 149.9 (46.7) 160.7 (17.1) | 1.5 | C | 159.4 (56.4) | Remained crystalline |

What is claimed:

1. Crystalline ascomycin characterized by data selected from: a powder X-ray diffraction pattern with peaks at about 8.7, 11.8 and 14.3±0.2 degrees 2 theta; an FTIR spectra having peaks at about 3443, 1639, 1194 and 1092 cm$^{-1}$; and a DSC thermogram showing two endotherms at about 148-152° C. and at about 158-162° C.

2. The ascomycin of claim 1, characterized by the powder X-ray diffraction pattern with peaks at about 8.7, 11.8 and 14.3±0.2 degrees 2 theta.

3. The ascomycin of claim 1, further characterized by the powder X-ray diffraction pattern with peaks at about 10.4, 11.4, 12.7, 13.9, 17.1, 17.4, 19.2, and 20.0±0.2 degrees 2 theta.

4. The ascomycin of claim 3, wherein the powder X-ray diffraction pattern is as depicted in FIG. 1.

5. The ascomycin of claim 1, characterized by the FTIR spectrum having peaks at about 3443, 1639, 1194 and 1092 cm$^{-1}$.

6. The ascomycin of claim 5, further characterized by the FTIR spectrum having peaks at about 3665, 1740, 1723, 1691, 1640, 1280, 1194, 1173, 1038, 997, 926, 858, 785, 771, 722 and 686 cm$^{-1}$.

7. The ascomycin of claim 6, wherein the FTIR spectrum is as depicted in FIG. 10.

8. The ascomycin of claim 1, characterized by the DSC thermogram showing two endotherms at about 148-152° C. and at about 158-162° C.

9. The ascomycin of claim 8, wherein the DSC thermogram is as depicted in FIG. 4.

10. Crystalline ascomycin characterized by data selected from: a powder X-ray diffraction pattern with peaks at about 7.5, 14.7 and 19.2±0.2 degrees 2 theta; an FTIIR spectra having peaks at about 3442, 1639, 1196 and 1093 cm$^{-1}$; and a DSC thermogram showing one endothermic peak at about 152-155° C.

11. The ascomycin of claim 10, characterized by the powder X-ray diffraction pattern with peaks at about 7.5, 14.7 and 19.2±0.2 degrees 2 theta.

12. The ascomycin of claim 11, further characterized by the powder X-ray diffraction pattern with peaks at about 10.4, 11.4, 13.9, 15.4, 16.2, 17.4, 19.7, 21.4 and 23.8±0.2 degrees 2 theta.

13. The ascomycin of claim 12, wherein the powder X-ray diffraction pattern is as depicted in FIG. 2.

14. The ascomycin of claim 10, characterized by the FTIR spectrum having peaks at about 3442, 1639, 1196 and 1093 cm$^{-1}$.

15. The ascomycin Form B of claim 14, further characterized by the FTIR spectrum having peaks at about 3579, 1739, 1721, 1690, 1649, 1279, 1197, 1173, 1093, 1037, 996, 928, 857 and 722 cm$^{-1}$.

16. The ascomycin Form B of claim 15, wherein the FTIR spectrum is as depicted in FIG. 11.

17. The ascomycin of claim 10, characterized by the DSC thermogram showing one endothermic peak at about 152-155° C.

18. The ascomycin of claim 17, wherein the DSC thermogram is as depicted in FIG. 5.

19. Crystalline ascomycin characterized by data selected from: a powder X-ray diffraction pattern with peaks at about 6.6, 15.5 and 19.7±0.2 degrees 2 theta; FTIR spectra having peaks at about 3459, 1649, 1196 and 1094 cm$^{-1}$; and a DSC thermogram showing one endothermic peak at about 156-160° C.

20. The ascomycin of claim 19, characterized by the powder X-ray diffraction pattern with peaks at about 6.6, 15.5 and 19.7±0.2 degrees 2 theta.

21. The ascomycin of claim 19, further characterized by the powder X-ray diffraction pattern with peaks at about 10.4, 11.4, 13.9, 15.5, 17.4, 19.3, 23.9, 25.1 and 25.6±0.2 degrees 2 theta.

22. The ascomycin of claim 21, wherein the powder X-ray diffraction pattern is as depicted in FIG. 3.

23. The ascomycin of claim 19, characterized by the FTIR spectrum having peaks at about 3459, 1649, 1196 and 1094 cm$^{-1}$.

24. The ascomycin of claim 23, further characterized by the FTIR spectrum having peaks at about 3579, 3457, 1739, 1720, 1690, 1279, 1036, 995, 955, 928, 855, 789, 774, 721 and 682 cm$^{-1}$.

25. The ascomycin of claim 24, wherein the FTIR spectrum is as depicted in FIG. 12.

26. The ascomycin of claim 19, characterized by the DSC thermogram showing one endothermic peak at about 156-160° C.

27. The ascomycin of claim 26, wherein the DSC thermogram is as depicted in FIG. 6.

28. A process for preparing crystalline ascomycin comprising:
   a) combining ascomycin with a first polar organic solvent to obtain a solution;
   b) combining the solution with a second polar organic solvent and an antisolvent to form a mixture;
   c) maintaining the mixture until ascomycin crystallizes; and
   d) recovering the crystalline ascomycin.

29. The process of claim 28, wherein the crystalline ascomycin is Form A or Form C.

30. The process of claim 28, wherein the first polar organic solvent in step a) is selected from the group consisting of: ethyl acetate, methanol, ethanol, n-propanol, iso-propanol, n-butanol, iso-butanol, tert-butanol, 2-butanol, acetone, acetonitrile, tetrahydrofuran, isobutyl acetate, n-butyl acetate, ethylformate, n-propyl acetate, iso-propyl acetate, methy-ethyl ketone, and mixtures thereof.

31. The process of claim 30, wherein the first polar organic solvent is ethyl acetate.

32. The process of claim 28, wherein the temperature in step a) is elevated to not more than about 50° C.

33. The process of claim 28, wherein any particle in step a) is filtered or diluted.

34. The process of claim 28, wherein the solution in step a) has a concentration of about 0.06 g/mL to about 0.8 g/mL.

35. The process of claim 28, wherein the antisolvent in step b) is selected from the group consisting of: cyclohexane, hexane, heptane, n-octane, iso-octane, and methylcyclohexane.

36. The process of claim 35, wherein the antisolvent in step b) is cyclohexane.

37. The process of claim 28, wherein the second polar organic solvent in step b) is selected from the group consisting of: water, N,N-dimethylformamide, dimethylsulfoxide, dimethyl acetamide, N,N-diethylformamide, and mixtures thereof.

38. The process of claim 37, wherein the second polar organic solvent in step b) is water or N,N dimethylformamide.

39. The process of claim 28, wherein the antisolvent and the second polar organic solvent are added more or less simultaneously to the solution of ascomycin in the solvent.

40. The process of claim 28, wherein the reaction mixture in step c) is maintained at a temperature of about −15° C. to about 30° C.

41. The process of claim 40, wherein the reaction mixture in step c) is maintained at a temperature of about 0° C. to about 8° C.

42. A process for preparing crystalline ascomycin comprising: dissolving ascomycin in ethyl acetate; maintaining the solution at a temperature of about −20° C. to about 10° C.; and recovering crystalline ascomycin.

43. The process of claim 42, wherein the crystalline ascomycin is Form B.

44. The process of claim 42, wherein the solution is maintained at a temperature of about 0° C. to about 8° C.

45. A process for preparing the ascomycin of claim 19, comprising maintaining ascomycin Form A at a temperature of about 100° C. to about 160° C. for at least about 30 minutes.

46. The process of claim 45, wherein Form A is maintained at a temperature of about 150° C.

47. The process of claim 45, wherein Form A is maintained at the temperature for about 1 hour.

48. A solid pharmaceutical composition comprising a therapeutically effective amount of the ascomycin of claim 1, the ascomycin of claim 10 or the ascomycin of claim 19 and at least one excipient.

49. A method for treating a patient suffering from a bacterial infection, comprising the step of administering to the patient the pharmaceutical composition of claim 48.

50. A method for treating a patient suffering from atopic dermatitis, comprising the step of administering to the patient the pharmaceutical composition of claim 48.

51. A method for treating a patient in need of immunosuppressive therapy, comprising the step of administering to the patient the pharmaceutical composition of claim 48.

52. A liquid pharmaceutical composition in the form of a suspension, comprising a therapeutically effective amount of the ascomycin of claim 1, the ascomycin of claim 10 or the ascomycin of claim 19 suspended in a liquid carrier.

53. A method for treating a patient suffering from a bacterial infection, comprising the step of administering to the patient the pharmaceutical composition of claim 52.

54. A method for treating a patient suffering from atopic dermatitis, comprising the step of administering to the patient the pharmaceutical composition of claim 52.

55. A method for treating a patient in need of immunosuppressive therapy, comprising the step of administering to the patient the pharmaceutical composition of claim 52.

* * * * *